US010052085B2

(12) United States Patent
Angott et al.

(10) Patent No.: US 10,052,085 B2
(45) Date of Patent: Aug. 21, 2018

(54) DIAGNOSTIC ASSEMBLY AND METHOD INCLUDING COLD BARS FOR DETECTING A PRESENCE OF CANCER

(71) Applicants: Paul G. Angott, Bloomfield Hills, MI (US); Richard Farkas, Bloomfield Hills, MI (US); Ajay Mudunuri, Detroit, MI (US); Steven Henke, Canton, MI (US)

(72) Inventors: Paul G. Angott, Bloomfield Hills, MI (US); Richard Farkas, Bloomfield Hills, MI (US); Ajay Mudunuri, Detroit, MI (US); Steven Henke, Canton, MI (US)

(73) Assignee: First Sense Medical, LLC, Mesa, AZ (US)

( * ) Notice: Subject to any disclaimer, the term of this patent is extended or adjusted under 35 U.S.C. 154(b) by 1197 days.

(21) Appl. No.: 14/209,212

(22) Filed: Mar. 13, 2014

(65) Prior Publication Data

US 2014/0276091 A1 Sep. 18, 2014

Related U.S. Application Data

(60) Provisional application No. 61/779,571, filed on Mar. 13, 2013.

(51) Int. Cl.
*A61B 10/00* (2006.01)
*A61B 5/01* (2006.01)
(Continued)

(52) U.S. Cl.
CPC .......... *A61B 10/0041* (2013.01); *A61B 5/015* (2013.01); *A61B 5/4312* (2013.01);
(Continued)

(58) Field of Classification Search
CPC ..... A61B 10/0041; A61B 5/015; A61B 5/489; A61B 5/4312; A61F 2007/0075;
(Continued)

(56) References Cited

U.S. PATENT DOCUMENTS

| 4,019,772 A * | 4/1977 | Lee ..................... A61G 7/1019 296/20 |
| 4,428,382 A | 1/1984 | Walsall et al. |

(Continued)

FOREIGN PATENT DOCUMENTS

| WO | 9529652 A1 | 11/1995 |
| WO | 2001056527 A1 | 8/2001 |
| WO | 2009118721 A1 | 1/2009 |

OTHER PUBLICATIONS

International Search Report dated Aug. 12, 2014 (PCT/US2014/025847).

*Primary Examiner* — Bo J Peng
(74) *Attorney, Agent, or Firm* — Dickinson Wright PLLC

(57) ABSTRACT

A diagnostic assembly (30, 320) and method for detecting a presence of cancer in a breast of a patient. The diagnostic assembly (20, 320) comprises a frame (22, 322), at least one cold bar (26, 326, 426) supported by the frame (22, 322) for receiving a hand of the patient, and a temperature controller (72) in communication with the cold bar (26, 326, 426) to maintain a constant temperature of the cold bar (26, 326, 426). The method comprises the steps of cooling at least one hand of the patient and recording a test thermal image of the breast of the patient after the hand of the patient has been cooled. The step of cooling the hand of the patient includes receiving the hand of the patient on the cold bar (26, 326, 426) to transfer heat from the hand of the patient to the cold bar (26, 326, 426), and maintaining the cold bar (26, 326, 426) at a preselected temperature.

4 Claims, 10 Drawing Sheets

(51) Int. Cl.
*A61B 5/00* (2006.01)
*A61F 7/00* (2006.01)

(52) U.S. Cl.
CPC ...... *A61B 5/489* (2013.01); *A61F 2007/0036* (2013.01); *A61F 2007/0075* (2013.01); *A61F 2007/0086* (2013.01); *A61F 2007/0087* (2013.01); *A61F 2007/0093* (2013.01); *A61F 2007/0095* (2013.01)

(58) Field of Classification Search
CPC ...... A61F 2007/0086; A61F 2007/0087; A61F 2007/0093; A61F 2007/0095; A61F 2007/0036
See application file for complete search history.

(56) References Cited

U.S. PATENT DOCUMENTS

| | | |
|---|---|---|
| 4,548,212 A | 10/1985 | Leung |
| 6,047,422 A | 4/2000 | Yousif |
| 6,077,228 A | 6/2000 | Schonberger |
| 6,199,233 B1 | 3/2001 | Kantrowitz et al. |
| 7,154,397 B2 | 12/2006 | Zerhusen et al. |
| 7,458,118 B2 | 12/2008 | Bak |
| 7,558,618 B1 | 7/2009 | Williams |
| 7,603,730 B2 | 10/2009 | Zelnik |
| 2004/0243202 A1* | 12/2004 | Lennox ............... A61F 7/0085 607/104 |
| 2005/0103353 A1* | 5/2005 | Grahn .................. A61F 7/02 128/898 |
| 2006/0026762 A1 | 2/2006 | Hornbach et al. |
| 2007/0058845 A1 | 3/2007 | Diakides et al. |
| 2008/0077005 A1 | 3/2008 | Piron et al. |
| 2008/0260225 A1 | 10/2008 | Szu |
| 2010/0312136 A1 | 12/2010 | Cozzie |
| 2010/0324379 A1 | 12/2010 | Clark et al. |
| 2011/0021944 A1* | 1/2011 | Arnon .................. A61B 5/015 600/549 |
| 2011/0091018 A1 | 4/2011 | Tybinkowski et al. |
| 2013/0317578 A1* | 11/2013 | Diller .................. A61B 5/01 607/104 |

* cited by examiner

DIAGNOSTIC ASSEMBLY AND METHOD INCLUDING COLD BARS FOR DETECTING A PRESENCE OF CANCER

CROSS REFERENCE TO RELATED APPLICATION

This application claims the benefit of U.S. provisional patent application Ser. No. 61/779,571 filed Mar. 13, 2013, and entitled "Cold Bar for FSM Tester".

BACKGROUND OF THE INVENTION

1. Field of the Invention

A diagnostic assembly and method for detecting a presence of cancer in a breast of a patient.

2. Description of the Prior Art

It has been recognized in the field of cancer research and treatment that blood vessels that feed cancerous tumors in breasts, i.e. angiogenic blood vessels, have a different anatomical structure than normal blood vessels, causing such angiogenic blood vessels to constrict to a lesser degree than normal blood vessels in response to a cold stimulus that is applied to the body of a patient. As such, the temperature associated with normal blood vessels decreases to a greater extent than angiogenic blood vessels when the body of the patient is exposed to the cold stimulus.

In recognition of this difference, a method called a "cold challenge" has been developed to detect the presence of breast cancer in patients, wherein thermal images of the breasts of the patient are recorded before and after the hands of the patient are subject to a cold stimulus. The second thermal image, i.e. a test thermal image, taken after the hands of the patient are subject to the cold stimulus, is compared to the first thermal image, i.e. a control thermal image, taken before the hands of the patient are subject to the cold stimulus to identify regions of the breasts in which the temperature remained substantially unchanged after the patient was subjected to the cold stimulus, therefore indicating the presence of angiogenic blood vessels and cancer in the regions.

One example of such a cold challenge assembly and method is disclosed in U.S. Pat. No. 7,558,618 to Darin S. Williams including a frame supporting a bucket of ice water, wherein thermal images of the breasts of the patient are recorded before and after the hands of the patient are cooled by dipping the hands of the patient in the bucket of ice water.

Such prior art cold challenges suffer from certain drawbacks. One such drawback is that the ice water tends to be heated by the hands of the patient during administration of the tests, especially at the boundary layer of the ice water around the patient's hands and fingers. Additionally, the temperature of the ice water can vary as it sits between and during the administration of tests. Such variances in the temperature of the ice water during and between administration of tests can lead to imprecise and inconsistent test results. Additionally, certain patients are sensitive to the cold, such as those with Renaud's Syndrome, and can become uncomfortable during testing. Further, such ice buckets are prone to spilling during administration of the test and during movement between tests. Thus, a nurse or technician is required to clean up and maintain the ice buckets during and after each test.

SUMMARY OF THE INVENTION

The invention provides for a diagnostic assembly including at least one cold bar supported by the frame for receiving a hand of the patient, and a temperature controller in communication with the cold bar to maintain a constant temperature of the cold bar during the test.

The invention further provides for a method of detecting a presence of cancer wherein the step of cooling the hand of the patient further includes receiving the hand of the patient on a cold bar to transfer heat from the hand of the patient to the cold bar, and maintaining the cold bar at a preselected temperature during the step of cooling the hand of the patient.

Advantages of the Invention

Several advantages of one or more aspects of the invention are that more consistent and precise testing results are produced because the cold bar is maintained at a consistent temperature during and between administration of tests. Additionally, patients with various medical backgrounds are able to remain comfortable during testing as the cold bar is capable of being maintained at a range of different temperatures. Furthermore, the administration of tests is advantageously a clean process as compared to prior testing methods, as no fluids are used during testing and therefore there is no risk of splashing of fluids during and between the administration of tests.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE ENABLING EMBODIMENTS

Figure 1:
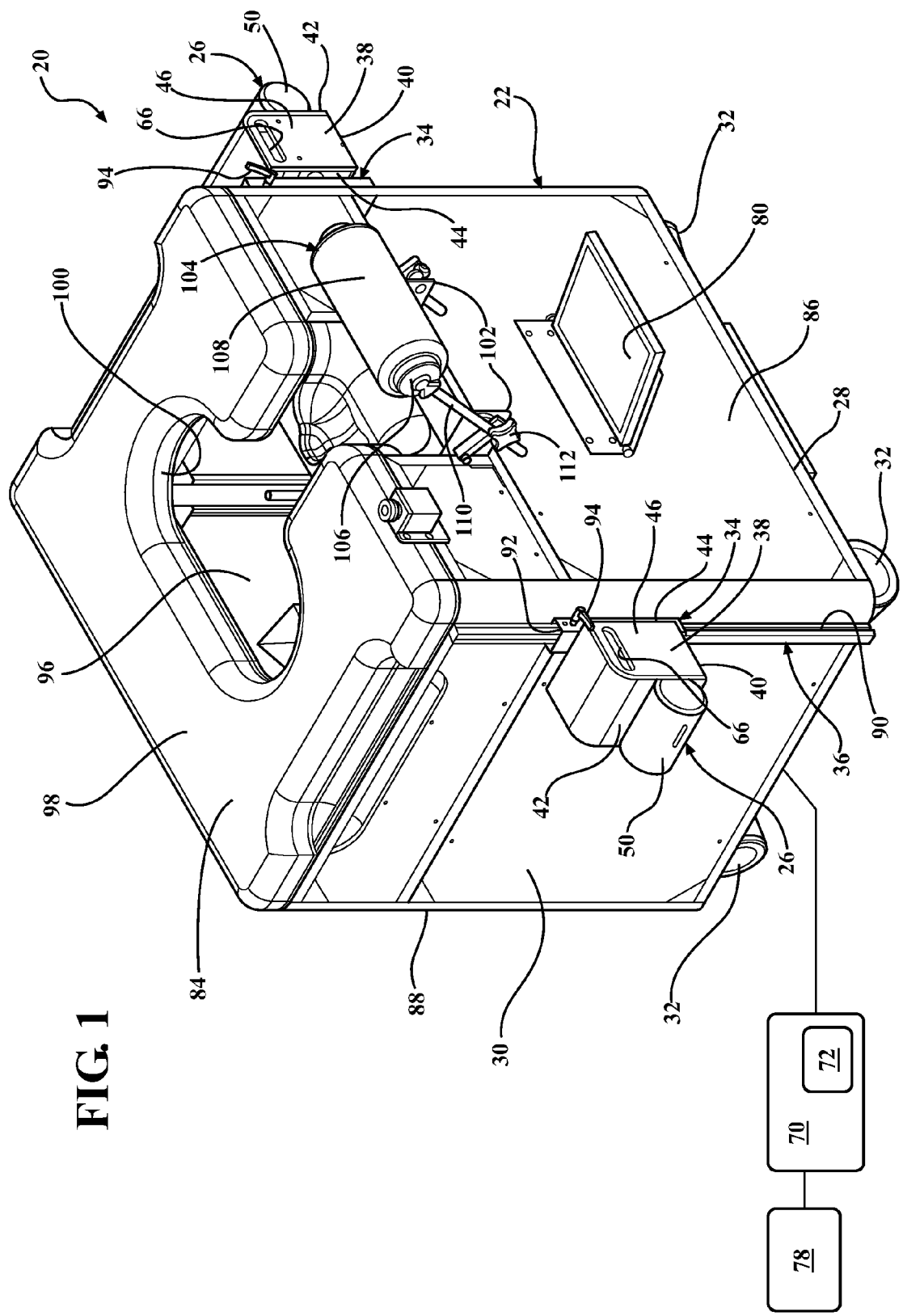
FIG. 1 is a perspective view of a first enabling embodiment of a diagnostic assembly for detecting a presence of cancer in a breast of a patient.

Referring to the figures, wherein like numerals indicate corresponding parts throughout the several views, a diagnostic assembly 20, 320 is generally shown for detecting a presence of cancer in a patient. The diagnostic assembly 20, 320 includes a frame 22, 322, generally indicated, for supporting the assembly 20, 320. A thermographic camera mechanism 324 is connected with the frame 22, 322 for recording thermal images of the breasts of the patient during testing with the assembly 20, 320. At least one cold bar 26, 326, 426, generally indicated, is connected with the frame 22, 322 for being received and gripped by the hands of the patient to cool the hands of the patient. As explained in greater detail below, the thermographic camera mechanism 324 is configured to record three dimensional thermal images of the breasts of the patient before and after the patient's hands are cooled by the cold bars 26, 326, 426, and the images are compared to one another to identify the presence of angiogenic blood vessels and cancerous regions of the breasts.

The frame 22, 322 includes a base 28, 328 and a pair of sidewalls 30, 330 that extend perpendicularly from said base 28, 328. A plurality of casters 32 are connected to the base 28, 328 for establishing rolling movement of the diagnostic assembly 20, 320 over a floor in an examination room. The frame 22, 322 further includes a carrier 34, 334, generally indicated, that is moveably connected with the base 28, 328. More specifically, a track 36, 336, generally indicated, extends perpendicularly to and away from the base 28, 328, and the carrier 34, 334 is slideably disposed on the track 36, 336 to interconnect the frame 22, 322 and carrier 34, 334 and to provide for vertical linear movement of the carrier 34, 334 along the track 36, 336.

Figure 2:
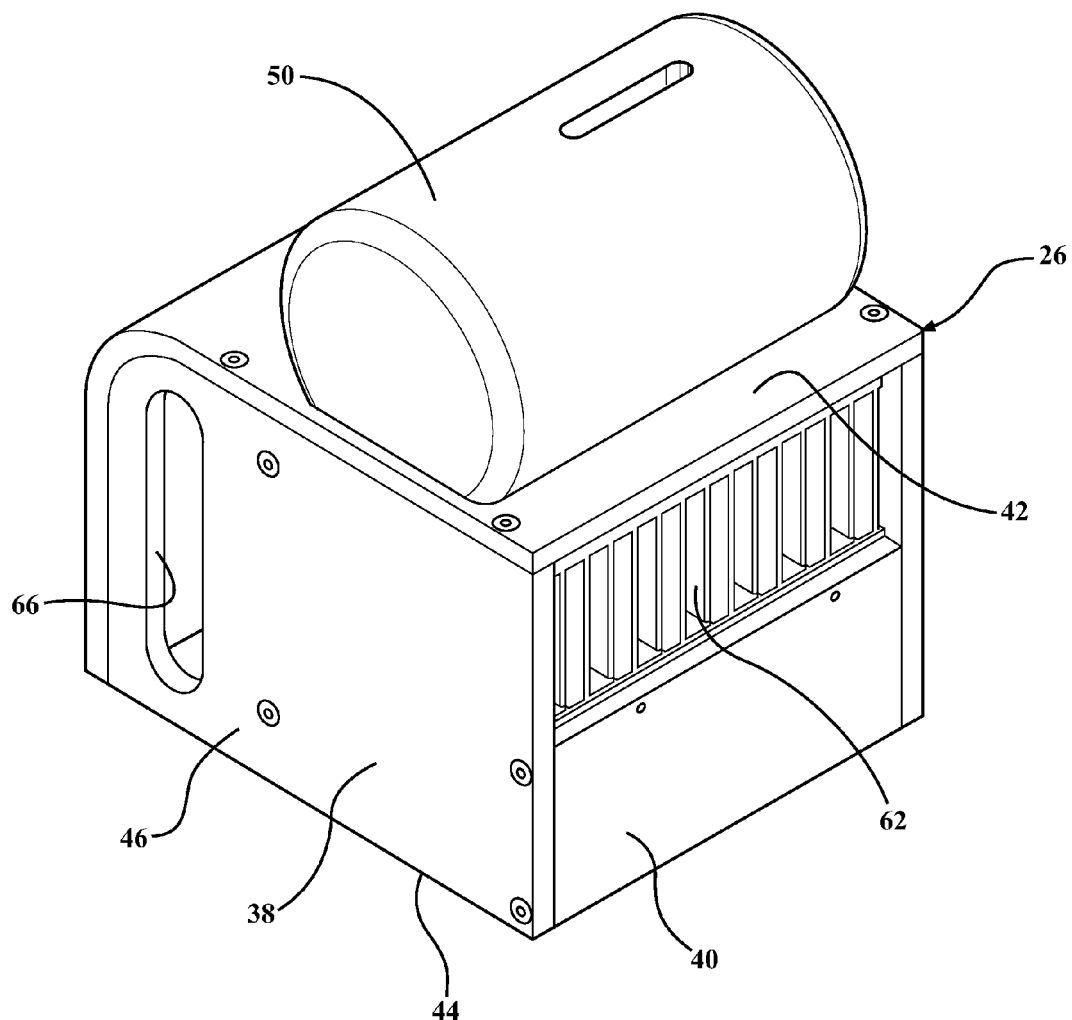
FIG. 2 is a perspective view of a first enabling embodiment of a cold bar.
Figure 7:
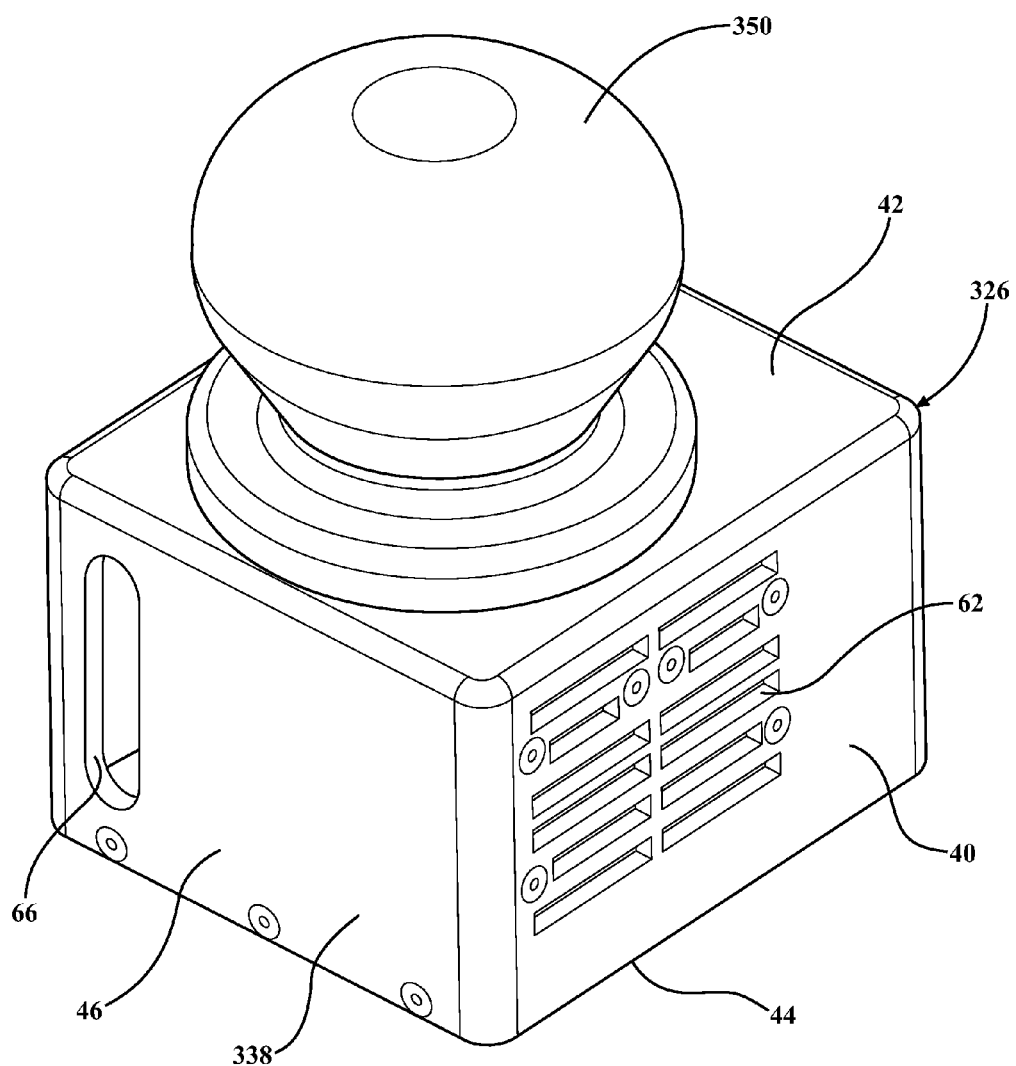
FIG. 7 is a perspective view of a second enabling embodiment of the cold bar illustrating a pommel having a generally spherical shape.

At least one cold bar 26, 326, 426 is connected with the carrier 34, 334 for cooling the hands of a patient during testing with the assembly 20, 320. As best presented in FIGS. 2 and 4, in the preferred embodiments, the at least once cold bar 26, 326, 426 includes a pair of cold bars 26, 326, 426 extending from the carrier 34, 334. As also presented in FIGS. 2, 3 and 7, each of the cold bars 26, 326, 426 includes a chassis 38, 338 that has a generally box shape. The chassis 38, 338 has a lower face 40, a frontward face 42 and a rearward face 44, a pair of side faces 46 that extend from the lower face 40, and a compartment 48 defined between the faces 40, 42, 44, 46. It should be appreciated that the chassis 38 could have other shapes such as, but not limited to, a spherical or ovoid shape.

The cold bars 26, 326, 426 each further include a pommel 50, 350, 450 of an aluminum material that is connected with the frontward face 42 of the chassis 38, 338 for being received and gripped by the hands of the patient. Each of the pommels 50, 350, 450 are spaced from the frame 22, 322, advantageously ensuring that that patient's arms are spaced from their breasts to prevent heating of the breasts by the arms during testing. As a result, the forced spacing of the patient's arms from the breasts prevents inaccurate and inconsistent measurements of the temperature of the breasts. It should be appreciated that the pommels 50, 350, 450 could be spaced from the frame 22, 322 at various distances as required to accommodate patients of various heights and having different arm lengths.

Figure 3:
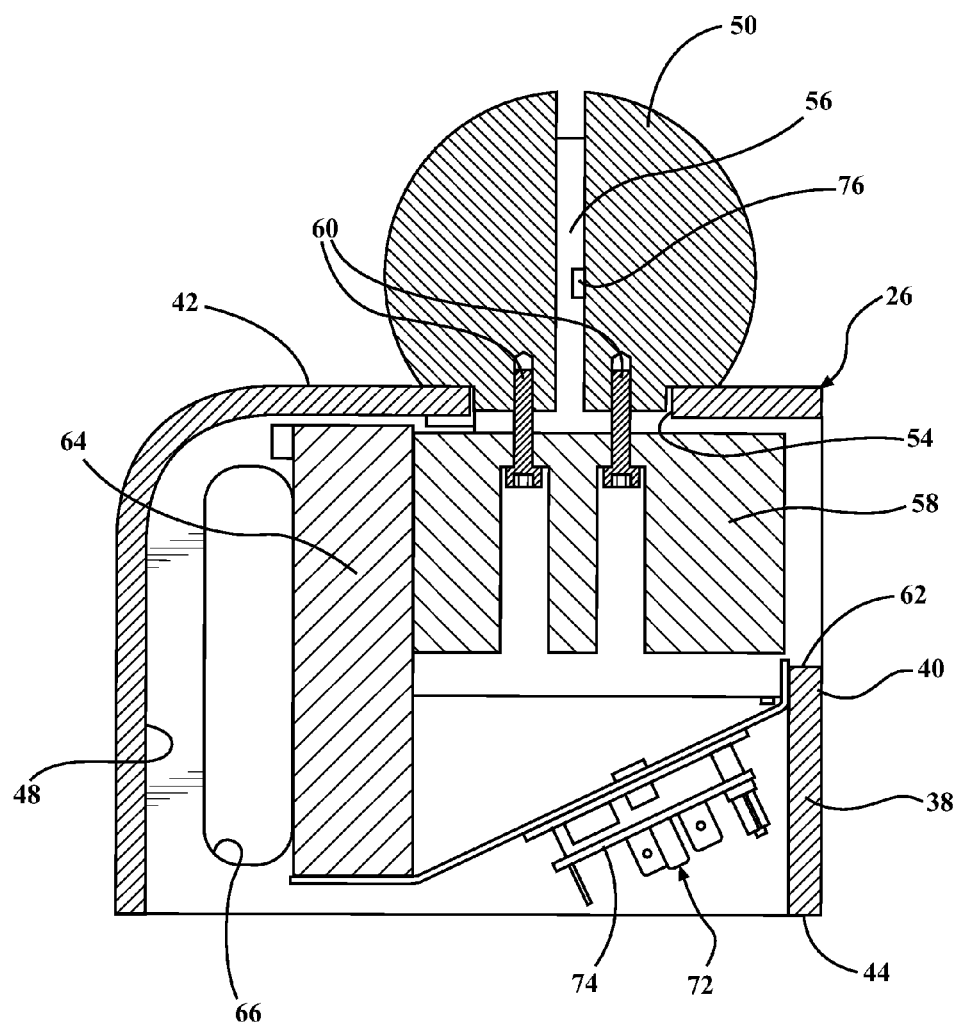
FIG. 3 is a cutaway side view of the first enabling embodiment of the cold bar.

As best presented in FIG. 3, the pommel 50, 350, 450 and the frontward face 42 of each of the chassis' 38, 338 define a passage 54 that extends to the compartment 48 of the chassis 38, 338. A cooling element 56 is disposed in the passage 54 in each of the pommels 50, 350, 450 for adjusting the temperature of the outer surface of the pommel 50, 350, 450. In the enabling embodiments, the cooling element 56 is of the peltier semiconductor type, i.e. a thermographic cooler, but it should be appreciated that other types of coolers could be used such as, but not limited to, a conventional refrigeration cycle. It should be appreciated that the cooling element 56 could extend across the length of the pommel 50, 350, 450 to ensure that the pommel 50, 350, 450 is evenly cooled across the length of the pommel 50, 350, 450. Alternatively, it should be appreciated that a plurality of cooling elements 56 could be placed at any area along the length of the pommel 50, 350, 450 to ensure that the pommel 50, 350, 450 is evenly cooled across the length of the pommel 50, 350, 450.

A heat sink 58 is disposed in the compartment 48 of each chassis 38, 338 adjacent to the cooling element 56 for directing heat produced by the cooling element 56 away from the cooling element 56. A pair of bolts 60 threadedly connect the pommel 50, 350, 450 and the heat sink 58 to sandwich the frontward face 42 of the chassis 38 between the pommel 50, 350, 450 and the heat sink 58 to secure the pommel 50, 350, 450, chassis 38, and heat sink 58 to one another. It should be appreciated that the pommel 50, 350, 450, chassis 38, and heat sink 58 could be fastened together in other ways such as, but not limited, through the use of screws or adhesives.

The lower face 40 of each chassis' 38, 338 defines a plurality of exhaust outlets 62 for allowing air that has been heated by the heat sink 58 to escape from the compartment 48. The exhaust outlets 62 of the chassis 38, 338 are advantageously pointed away from the pommels 50, 350, 450 to prevent heated air from blowing on the patient and the pommels 50, 350, 450. It should be appreciated that any number of exhaust outlets 62 could be present and they could be defined by other areas of the chassis 38, 338, but they should not be oriented toward the patient or pommels 50, 350, 450. A fan 64 is disposed in the compartment 48 adjacent to the heat sync for directing air that has been heated by the heat sink 58 out of the exhaust outlets 62. The side faces 46 of the chassis 38 each define an air inlet 66 for allowing ambient air to enter the compartment 48. It should be appreciated that any number of air inlets 66 could be defined by the chassis 38, 338 and they could be defined by other areas of the chassis 38, 338.

A controller 70 is connected with the assembly 20, 320 for controlling the assembly 20, 320 during administration of tests. The controller 70 includes a computer (not shown) that is connected with the frame 22, 322. It should be appreciated that the computer could be disposed inside or outside of the frame 22, 322 and can control various aspects of the assembly 20. The controller 70 includes a temperature controller 72 that is connected with the cooling element 56 to control the temperature of the pommels 50, 350, 450 of the cold bars 26, 326, 426. As best shown in FIG. 3, the temperature controller 72 includes a circuit board 74 that is disposed in the compartment 48 and electrically connected with the cooling element 56. A sensor 76 engages each of the pommels 50, 350, 450 for reading the temperature of the outer surface of the pommels 50, 350, 450 and transmitting temperature data. In the enabling embodiments, the sensor 76 is a thermistor, but it should be appreciated that other temperature sensors 76 could be used such as, but not limited to, a conventional resistance thermometer. The temperature controller 72 is electrically connected with the sensor 76 for receiving temperature data from the sensor 76 to allow the controller 70 to maintain a constant temperature of the outer surface of each of said pommels 50. Accordingly, a feedback based closed loop temperature regulator circuit is used to monitor and maintain a constant temperature. However, it should be appreciated that other circuits could be used to maintain the temperature of the pommels 50, 350, 450. Accordingly, it should be appreciated that the assembly 20, 320 advantageously provides for consistent testing results because the cold bars 26, 326, 426 are maintained at a consistent temperature during and between administrations of tests.

Figure 4:
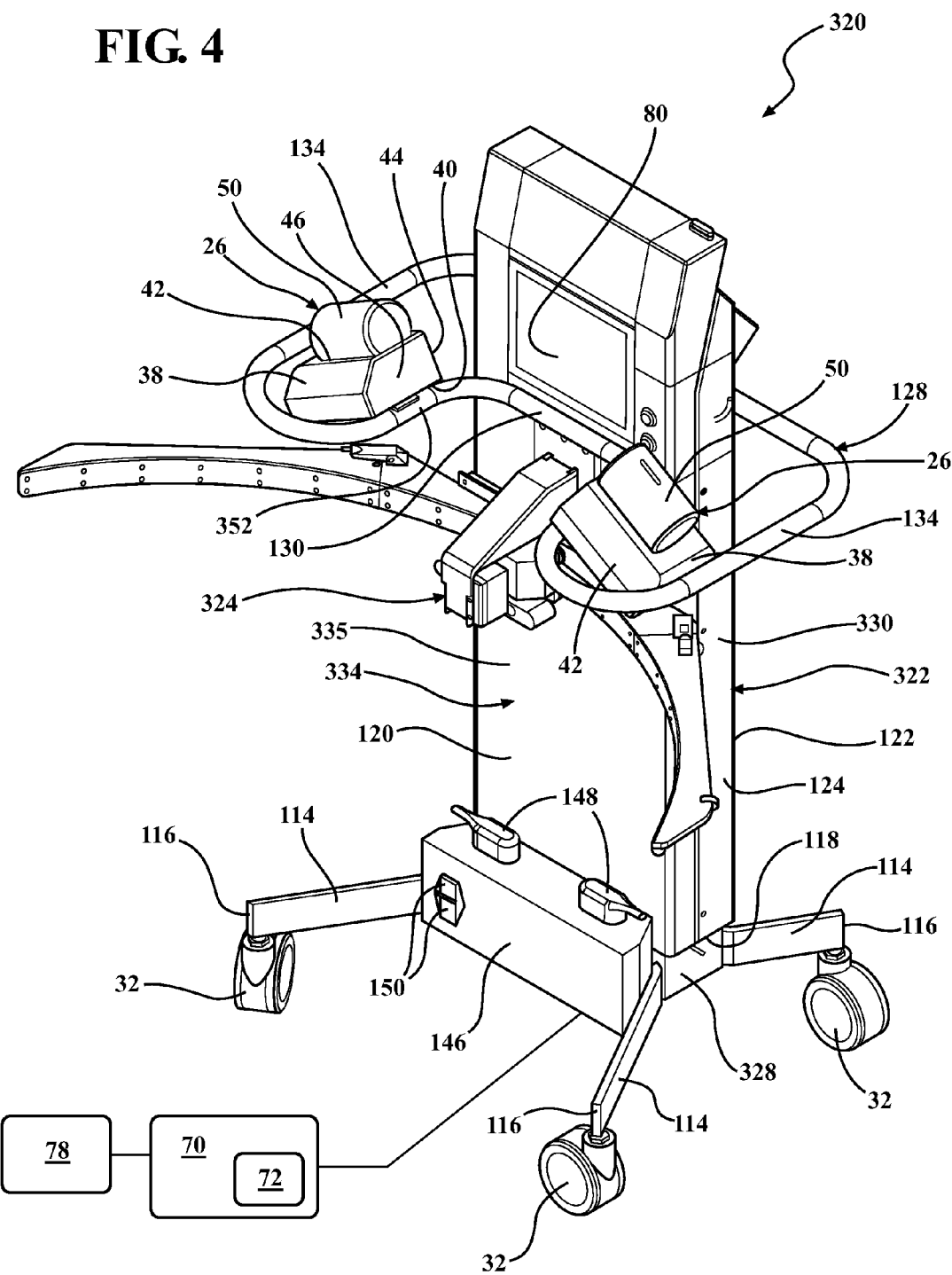
FIG. 4 is a perspective front view of a second enabling embodiment of the diagnostic assembly.

As best shown in FIGS. 1 and 4, a power source 78 is electrically connected with the cooling element 56, the temperature controller 72, and the sensor 76 for powering the cooling element 56, sensor 76 temperature controller 72. It should be appreciated that the power source 78 could be various types of batteries or a connection to a power outlet in a wall.

The thermographic camera mechanism 324 is connected with the carrier 34, 334 for measuring the temperature of the patient's breasts while the pommels 50, 350, 450 receive the gripped hands of the patient. The thermographic camera mechanism 324 is electrically connected with the power source 78 and the controller 70 for powering and controlling the thermographic camera mechanism 324.

A graphical user interface 80, 82 that has a rectangular shape is connected with the frame 22, 322 and is in data connection with the controller 70 for receiving and presenting operational data related to the assembly 20, 320 to the physician or patient. The graphical user interface, 80, 82 is electrically connected with the power source 78 for powering the graphical user interface. It should be appreciated that the graphical user interface could be various types of conventional interfaces such as, but not limited to, a conventional LCD monitor or cathode ray tube monitor. In the enabling embodiments, the graphical user interface 80, 82 is of the touch-screen type for receiving commands from the patient during administration of the exam and therefore the commands are transmitted to the controller 70 to adjust various parameters of the assembly 20, 320 such as the vertical height and temperature of the cold bars 26, 326, 426.

In the first enabling embodiment of the diagnostic assembly 20, as best presented in FIG. 1, the frame 22 further includes a top 84, a front wall 86, a rear wall 88, and the pair of sidewalls 30. The track 36 includes a pair of tracks 36 that each extend along one of the sidewalls 30 between the top 84 and the base 28 of the frame 22. Each of the tracks 36 defines a pair of slots 90 that extend therein in spaced and parallel relationship with one another and linearly along the track 36.

The carrier 34 includes a pair of carriers 34 that each have a generally U-shaped cross section and partially surround one of the tracks 36. The carriers 34 each include a pair of projections 92 that are each slideably disposed in one of the slots 90 of the track 36 for allowing the vertical movement of the carrier 34 and the cold bar 26 along the track 36, and for preventing outward movement of the carrier 34 and the cold bars 26 relative to the track 36. A pin 94 slideably extends through each carrier 34 for engaging one of the tracks 36 to lock the carrier 34 and the cold bars 26 in a predetermined vertical location along the track 36. Accordingly, a physician is able to slide the carriers 34 and cold bars 26 along the tracks 36 to a location that suits the height and arm length of the patient, and then lock the carrier 34 in place using the pin 94.

The frame 22 defines a chamber 96 between the top 84, base 28, front wall 86, rear wall 88 and sidewalls 30. The top 84 is defined by a padding layer 98 for allowing a patient to comfortably lie along the top 84 of the frame 22. It should be appreciated that the padding could be made of various materials such as, but not limited to, a foam material. The top 84 further defines an opening 100 that extends to the chamber 96 for receiving the breasts of the patient. The thermographic camera mechanism (not expressly shown) is disposed inside the frame 22.

A pair of flanges 102 that have a rectangular shape extend away from the front wall 86 of the frame 22 in spaced and parallel relationship with one another. A head rest 104 is connected with and spaced from the flanges 102 of the frame 22 for receiving the head of a patient lying along the top 84 of the frame 22. The head rest 104 includes an inner cylinder 106 that has a tube shape, and a cushion 108 that has a tube shape disposed about the inner cylinder 106. A pair of rods 110 are each pivotally connected with one of the flanges 102 and the head rest 104 for facilitating a pivoting movement of the head rest 104 toward and away from the front wall 86 of the frame 22 relative to the flanges 102. A pair of fasteners 112 each threadedly extend through one of the flanges 102 and one of the rods 110 for tightening the head rest 104 in a fixed position. Accordingly, a physician may pivot and secure the head rest 104 to a position that is comfortable for the patient while they lie along the top 84 of the frame 22. It should be appreciated that the head rest 104 could be of other types such as, but not limited to, a member that extends away from the front wall 86 of the frame 22.

The graphical user interface 80 includes a first graphical user interface 80 that extends perpendicularly from the front wall 86 and is spaced from the flanges 102 toward the bottom such that it may be used to present and receive operational data to and from the patient while the patient is lying along the top 84 of the frame 22. Further, the rearward face 44 of each of the chassis' 38 is connected with the carrier 34 to provide for movement of the cold bars 26 along the track 36.

Figure 5:
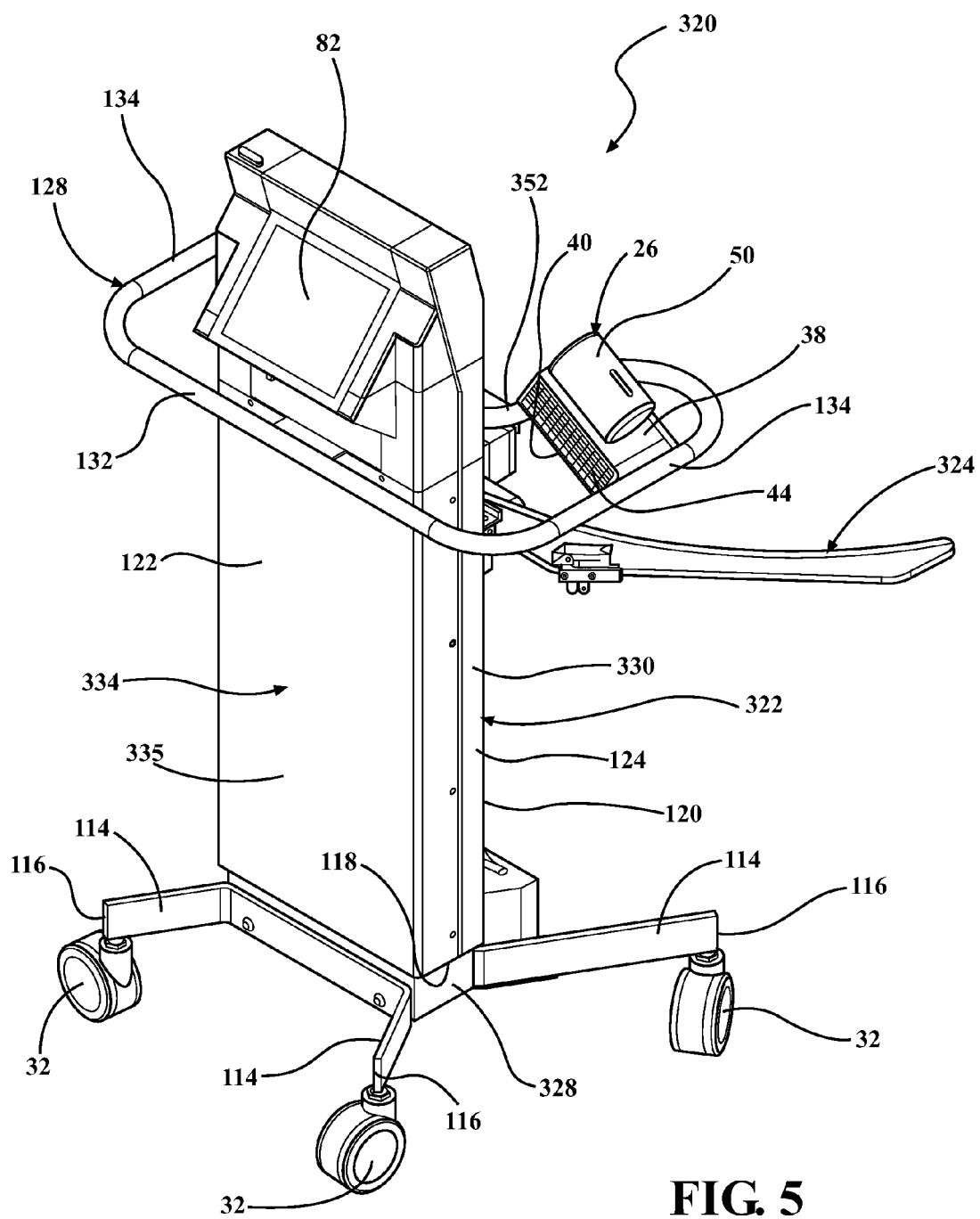
FIG. 5 is a perspective back view of the second enabling embodiment of the diagnostic assembly.
Figure 6:
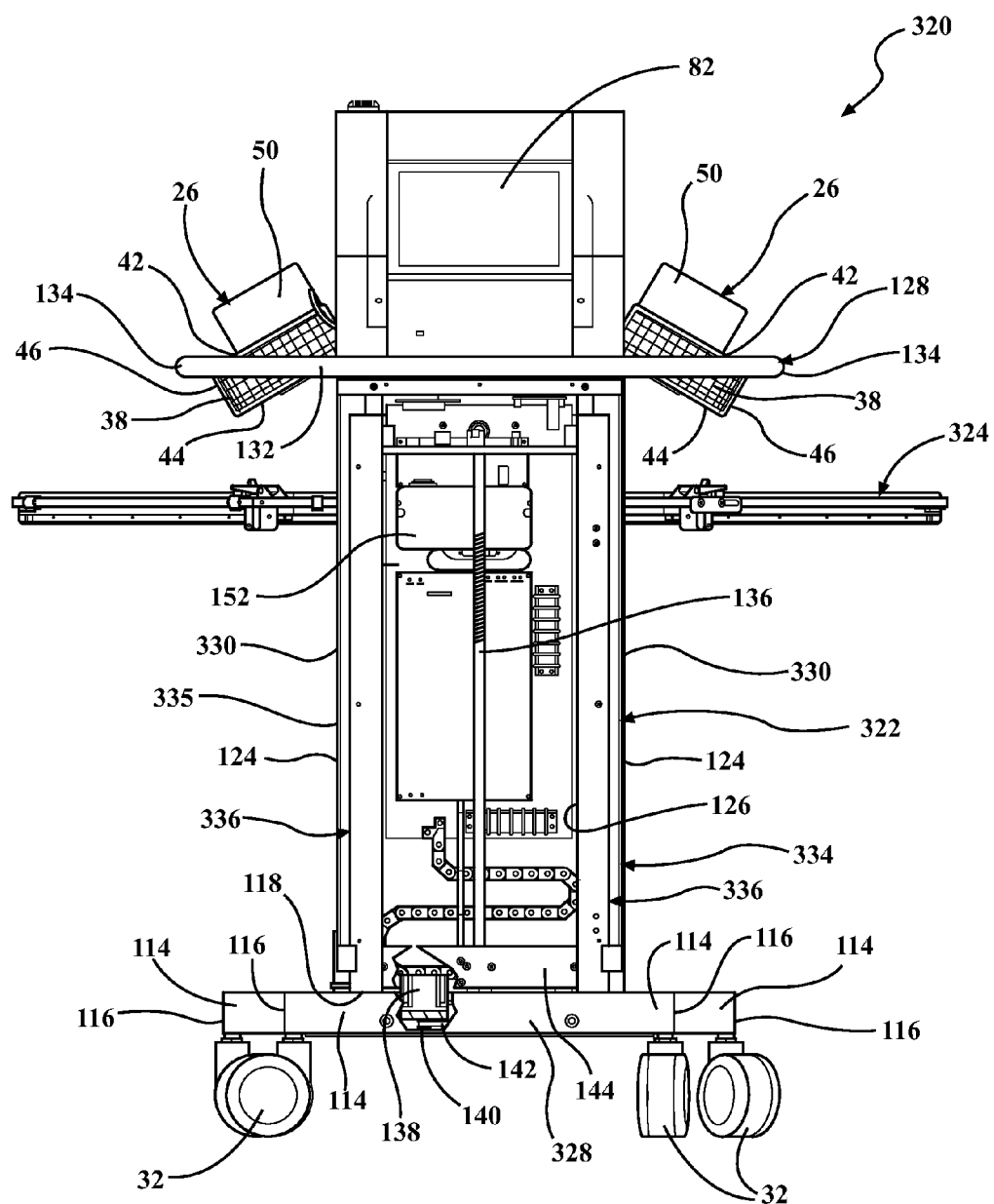
FIG. 6 is a cutaway back view of the second enabling embodiment of the diagnostic assembly presenting tracks and a lead screw for vertically moving a pair of cold bars.

In the second enabling embodiment of the diagnostic assembly 320 as best presented in FIGS. 4-6, the assembly 320 further includes a plurality of legs 114 that each have a terminal end 116 and extend outwardly from the base 328 of the frame 322 to the terminal end 116. One of the casters 32 is connected to each of the legs 114 adjacent to the terminal end 116. It should be appreciated that any number of legs 114 could be used and that the legs 114 could extend to various lengths.

Further, the track 336 includes a pair of beams 336 that extend perpendicularly from the base 28 of the frame 22 in spaced and parallel relationship with one another. The carrier 334 includes a case 335 that has a generally cuboid shape and has a bottom periphery 118, front periphery 120, a rear periphery 122, and a pair of side peripheries 124 extending between the bottom, front, and rear peripheries 118, 120, 122. The bottom periphery 118 defines a channel 126 that extends therein and telescopically receives the beams 336 to provide for vertical and linear movement of the case 335 along the beams 336.

The carrier 334 further includes a handle 128, generally indicated, that has a ring-shaped cross-section and extends about the case 335. The handle 128 includes a front section 130 that engages the front periphery 120 of the case 335, a rear section 132 that is spaced from the rear periphery 122 of the case 335, and a pair of side sections 134 that are each spaced from one of the side peripheries 124 of the case 335. The handle 128 defines a hollow that extends therethrough. The front section 130 of the handle 128 has a U-shape that extends along a pair of limbs 352 toward the front face of the support. The rearward face 44 of each of the cold bars 326 engages one of the limbs 352 of the front section 130 of the handle 128 to space the pommels 350 from the case 335. It should be appreciated that the handle 128 advantageously serves as a grip for allowing a physician or patient to move the assembly 320, as a support for the cold bars 326, and as a bumper for protecting the assembly 320 during movement of the assembly 320.

The graphical user interface 80, 82 includes a first graphical user interface 80 that is connected with the front periphery 120 of the case 335 and a second graphical user interface 82 that is connected with the rear periphery 122 of the case 335. Accordingly, it should be appreciated that a patient and physician could each receive and input data during administration of an exam at the same time through the first and second graphical user interfaces 80, 82.

The thermographic camera mechanism 324 is connected with the front periphery 120 of the case 335 and is spaced from the first graphical user interface 80 toward the bottom periphery 118 for taking thermographic images of the breasts of the patient.

As best presented in FIG. 6, a lead screw 136 that is threaded is rotatably connected with and extends perpendicularly from the base 328 between the beams 336. A driving motor 138 engages the base 328. The driving motor 138 includes a piston 140 that is rotatably connected with the lead screw 136 for providing rotary motion of the lead screw 136. A belt 142 is disposed about the piston 140 of the driving motor 138 and the lead screw 136 for transferring rotating movement of the piston 140 to the lead screw 136.

The case 335 includes a cross-member 144 that has a cuboid shape and extends transversely between the side peripheries 124 at the bottom periphery 118 of the case 335. The lead screw 136 threadedly extends through the cross-member 144 for converting rotary motion of the lead screw 136 into vertical and linear motion of the cross-member 144 along the lead screw 136 to provide for vertical and linear movement of the carrier 334. It should be appreciated that the case 335 could have other shapes such as, but not limited to an ovoid shape.

The controller 70 is further in data communication with the driving motor 138 for controlling the driving motor 138 to control the vertical and linear movement of the carrier 34. The power source 78 is further electrically connected with the driving motor 138 for powering the driving motor 138.

As best presented in FIG. 4, a power container 146 that has a rectangular shape is connected to the frame 322 adjacent to the front periphery 120 of the case 335. A pair of hooks 148 extend from the power container 146 in spaced and parallel relationship with one another for receiving a wrapped power cable. The power source 78 includes a pair of power sockets 150 that are defined by the power container 146 for electrically connecting the assembly 320 with a wall socket. The power source 78 further includes a backup battery 152 that engages the case 335 and is electrically connected with the controller 70, cold bars 26, and the thermographic camera mechanism 324 for providing for backup power of the controller 79, cold bars 26, and the thermographic camera mechanism 324.

Figure 8:
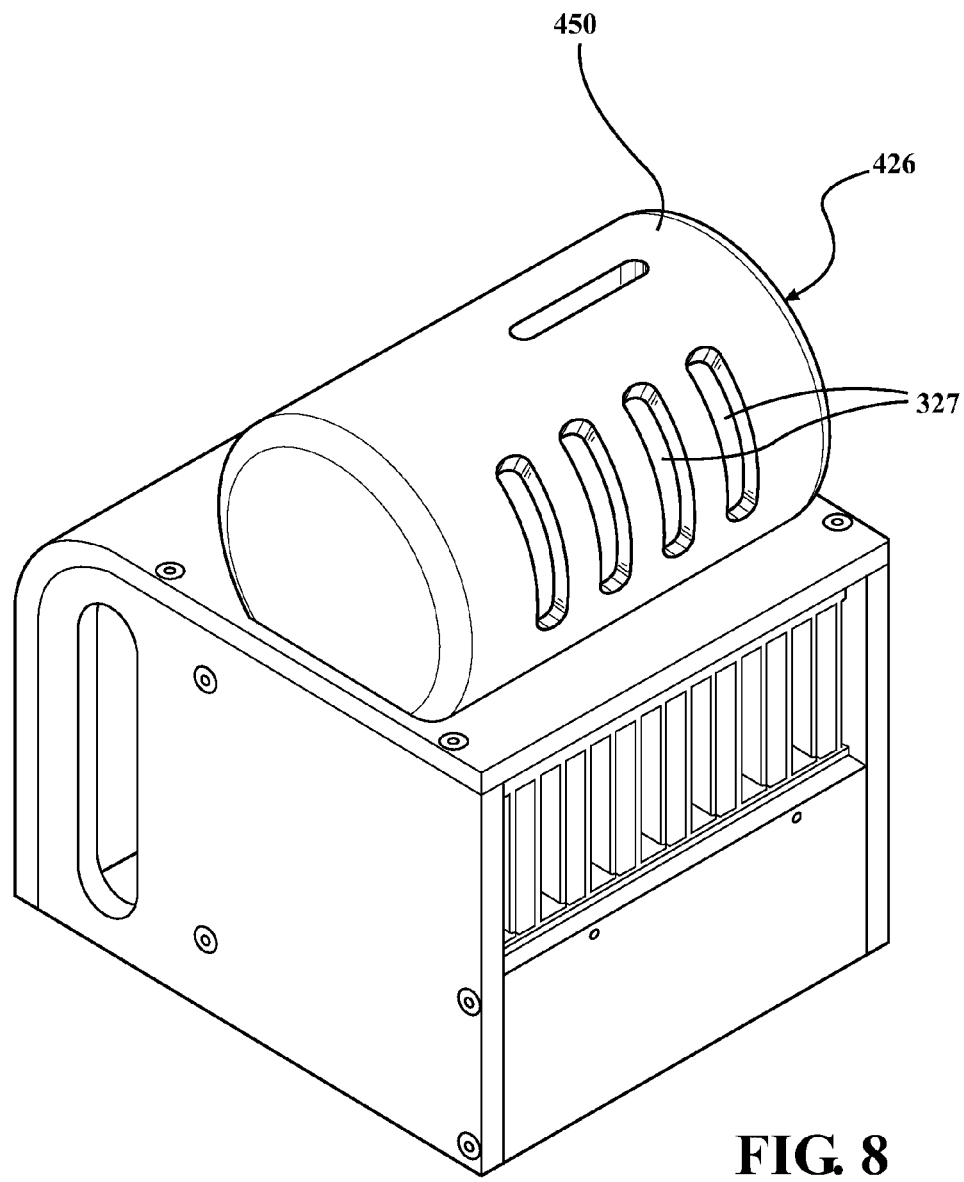
FIG. 8 is a perspective view of a third enabling embodiment of the cold bar illustrating the pommel defining a plurality of indentations for receiving the fingers of a patient.
Figure 9:
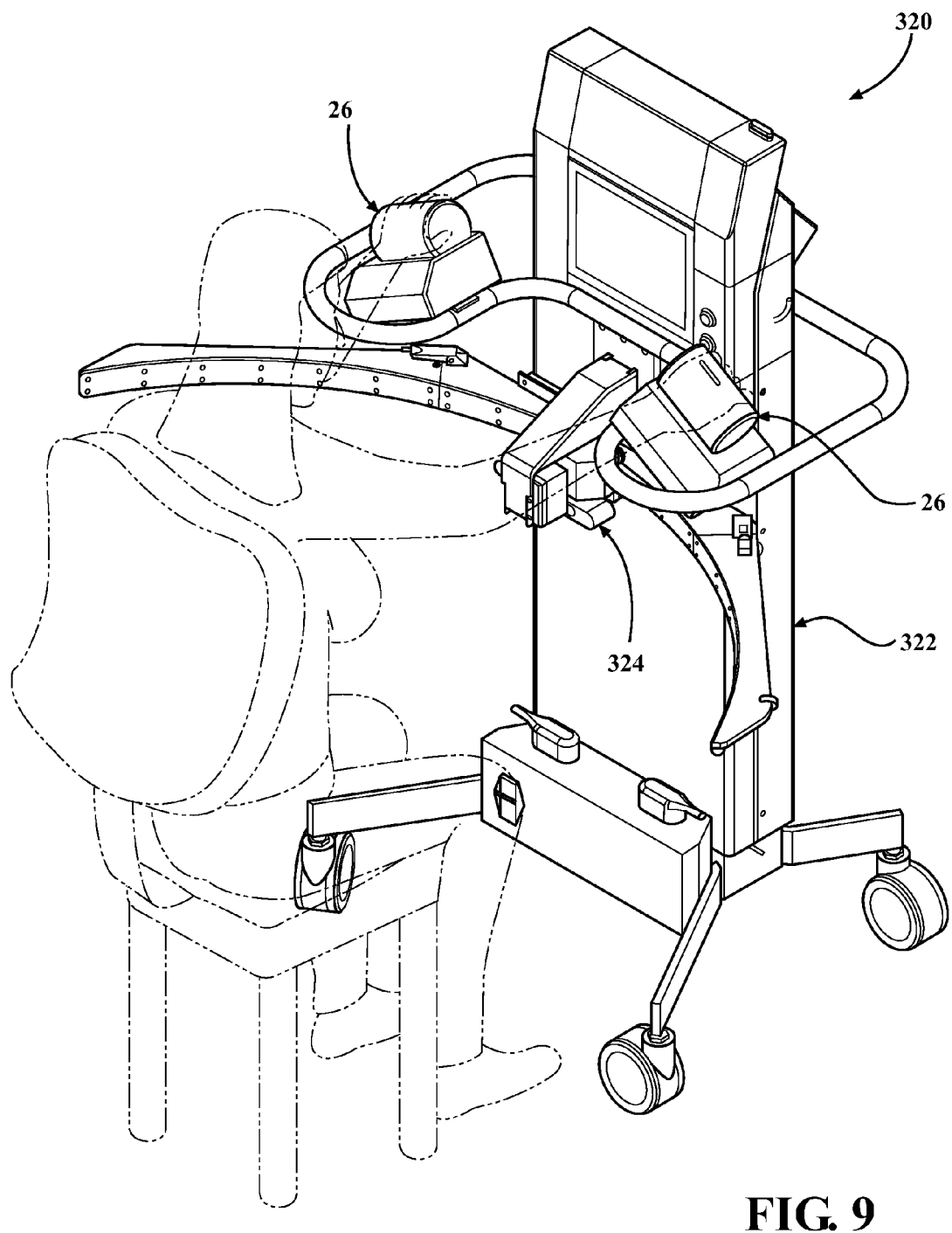
FIG. 9 is a perspective view of the second enabling embodiment of the diagnostic assembly illustrating a patient gripping the cold bars.

In the first and second enabling embodiments of the cold bar 26, 326, 426, the pommels 50 have a generally cylindrical shape. However, it should be appreciated that the pommels 50 could have other shapes to increase the surface area of the pommels 50 while they receive gripped hands of the patient and to make the pommels 50 more comfortable to grip. In a further enabling embodiment of the pommels 350 as best presented in FIG. 7, each of the pommels 350 has a generally spherical shape. As best presented in FIG. 8, each of the pommels 50, 350, 450 could further define a plurality of indentations for receiving individual fingers of the patient to increase the surface area of the pommels 50, 350, 450 that is received by the gripped hand of the patient.

Figure 10:
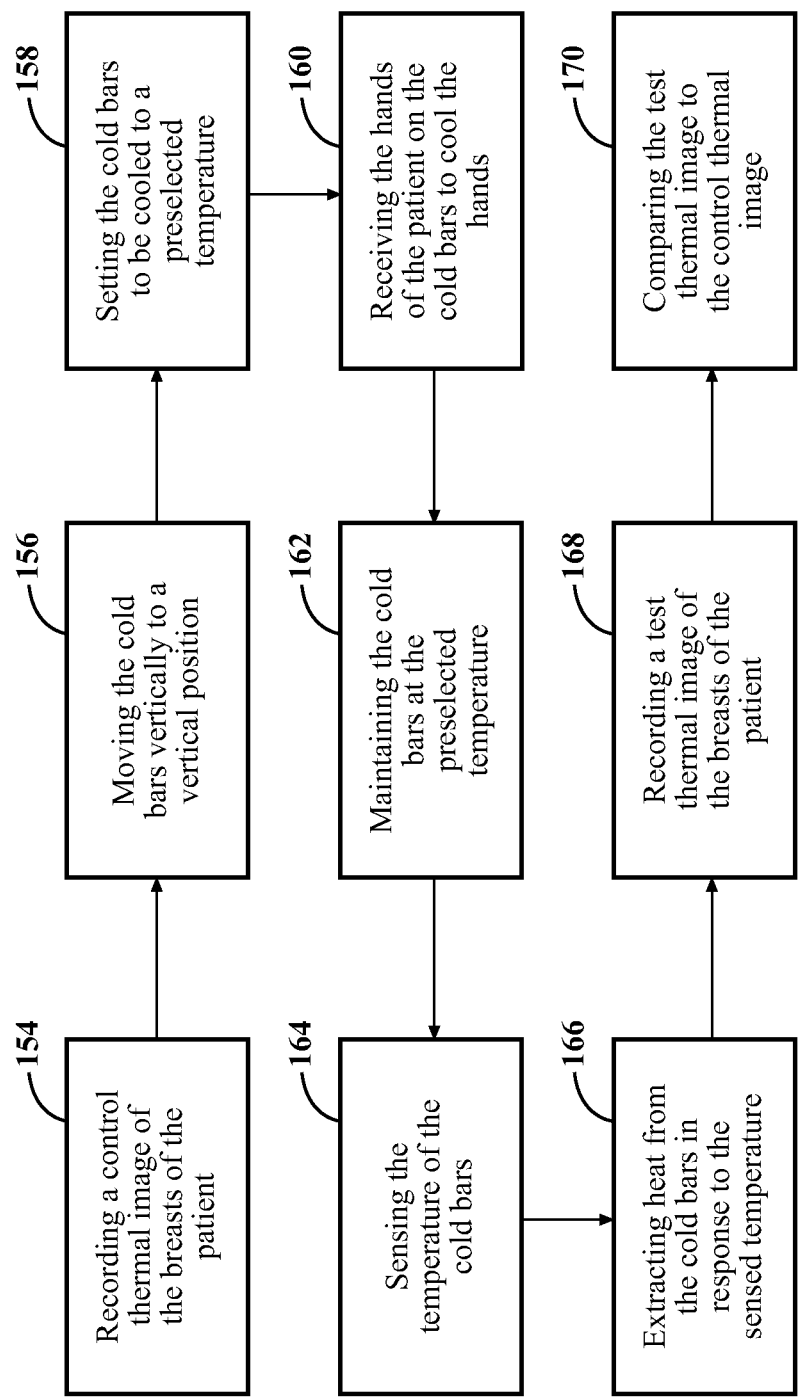
FIG. 10 is a flowchart a method for detecting a presence of cancer in breasts of a patient.

As best presented in FIG. 10, a method for detecting a presence of cancer in breasts of a patient using at least one cold bar 26, 326, 426 is also disclosed. The method comprises the step of 154 recording a control thermal image of the breasts of the patient using the thermographic camera mechanism 324. In the enabling embodiment, the control thermal image is a three-dimensional image, however, it should be appreciated that a two-dimensional thermal image could also be recorded by the thermographic camera mechanism 324. The control thermal image is recorded prior to cooling of the hands of the patient to establish a thermal image of the breasts of the patient in a state in which a cold stimulus has not been applied to the patient.

The method proceeds by 156 moving the cold bars 26, 326, 426 vertically to a vertical position to accommodate for the height and arm length of the patient to provide for increased comfort of the patient and to maintain the arms of the patient in a position spaced from the breasts of the patient. In the enabling embodiments, the cold bars 26, 326, 426 are moved vertically by sliding the carrier 34, 334 along the track 36, 336, but it should be appreciated that the cold bars 26, 326, 426 could be moved in other ways such as, but not limited to, by placing the cold bars, 26, 326 on a table or other surface that is positioned at a desired vertical position. It should also be appreciated that while moving the cold bars 26, 326, 426 vertically to a vertical position, the arms of the patient should also be spaced horizontally from the breasts of the patient. Accordingly, the arms of the patient are spaced from the breasts of the patient prior to recording both the control and test thermal images to prevent inaccurate test results.

The method proceeds by 158 setting the cold bars 26, 326, 426 to be cooled to a preselected temperature. It is advantageous that the cold bars 26, 326, 426 can be set to various temperatures to maintain comfort of patients with different medical backgrounds during administration of the test. For most patients, the preselected temperature is in the range between 10 and 12 degrees Celsius (50 to 53.6 degrees Fahrenheit). However, it should be appreciated that a warmer preselected temperature can be chosen for patients with certain medical backgrounds. For example, patients with Renaud's syndrome who are sensitive to cold temperatures can undergo testing at a higher temperature, like 17 degrees Celsius (62.6 degrees Fahrenheit).

The method then proceeds by 160 cooling the hands of the patient. More specifically, as best presented in FIG. 8, the hands of the patient are cooled by respectively receiving gripped hands of the patient on the cold bars 26, 326, 426 to transfer heat from the hands of the patient to the cold bars 26, 326, 426.

Additionally, the method includes the step of 162 maintaining the cold bars 26, 326, 426 at the preselected temperature during the step of cooling the hands of the patient. The step of 162 maintaining the cold bars 26, 326, 426 at the preselected temperature includes the step of 164 sensing the temperature of the cold bars 26, 326, 426 during the transferring of heat from the hands of the patient to the cold bars 26, 326, 426 and the step of 166 extracting heat from the cold bars 26, 326, 426 in response to the sensed temperature of the cold bars 26, 326, 426.

After the hands of the patient have been cooled, the method proceeds by 168 recording a test thermal image of the breasts of the patient to capture temperature changes in regions of the breasts of the patient in response to cooling of the hands of the patient.

The method also includes the step of 170 comparing the test thermal image to the control thermal image to identify regions of the breasts in which the temperature remained substantially unchanged after the hands of the patient were cooled indicating the presence of angiogenic blood vessels and cancer in the regions. Typically regions that have dropped approximately 0.2 degrees Fahrenheit are identified as indicators of breast cancer, however other temperature changes could be identified.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. A diagnostic assembly (20, 320) for detecting a presence of cancer in a patient comprising:
    a frame (22, 322) including a base (28, 328) and a pair of sidewalls (30, 330) extending perpendicularly from said base (28, 328),
    a plurality of casters (32) connected to said base (28, 328) for establishing rolling movement of said diagnostic assembly (20, 320) over a floor in an examination room,
    said frame (22, 322) further including a carrier (34, 334) moveably connected with said base (28, 328),
    a track (36, 336) extending perpendicularly to and away from said base (28, 328) interconnecting said base (28, 328) and said carrier (34, 334),
    said carrier (34, 334) slideably disposed on said track (36, 336) to provide for vertical and linear movement of said carrier (34, 334) along said track (36, 336),
    a pair of cold bars (26, 326, 426) connected with said carrier (34, 334) and spaced from said track (36, 336),
    each of said cold bars (26, 326, 426) including a chassis (38, 338) having a lower face (40) and a frontward face (42) and a rearward face (44) and a pair of side faces (46) extending from said lower face (40) and defining a compartment (48) between said faces (40, 42, 44, 46),
    said cold bars (26, 326, 426) each further including a pommel (50, 350, 450) of an aluminum material connected with said frontward face (42) of said chassis (38, 338) for receiving a hand of the patient,
    said pommel (50, 350, 450) of each of said cold bars (26, 326, 426) being spaced from said carrier (34, 334) by said chassis (38, 338),
    said pommel (50, 350, 450) and said frontward face (42) of said chassis (38, 338) of each of said cold bars (26, 326, 426) defining a passage (54) extending to said compartment (48) of said chassis (38, 338),
    a cooling element (56) disposed in said passage (54) in each of said pommels (50, 350, 450) for adjusting the temperature of said outer surface of said pommel (50, 350, 450),
    said cooling element (56) being of the peltier semiconductor type,
    a controller (70) connected with said assembly (20, 320) for controlling said assembly (20, 320),
    said controller (70) including a temperature controller (72) connected with said cooling element (56) to control the temperature of said outer surface of said pommels (50, 350, 450),
    said temperature controller (72) including a circuit board disposed in said compartment (48) and electrically connected with said cooling element (56) to control the temperature of said outer surface of said cold bars (26, 326, 426),
    a sensor (76) engaging each of said pommels (50, 350, 450) for reading the temperature of said outer surface of said pommels (50, 350, 450) and transmitting temperature data,
    said controller (70) being electrically connected with said sensor (76) for receiving temperature data from said sensor (76) to allow said controller (70) to maintain a constant temperature of said outer surface of each of said pommels (50, 350, 450),
    a heat sink (58) disposed in said compartment (48) adjacent to said cooling element (56) for directing heat produced by said cooling element (56) away from said cooling element (56),
    a pair of bolts (60) threadedly connecting said pommel (50, 350, 450) and said heat sink (58) to sandwich said frontward face (42) of said chassis (38, 338) between said pommel (50, 350, 450) and said heat sink (58) to secure said pommel (50, 350, 450) and said chassis (38, 338) and said heat sink (58) to one another,
    said lower face (40) of said chassis (38, 338) defining a plurality of exhaust outlets (62) for allowing heated air adjacent to said heat sink (58) to escape from said compartment (48),
    a fan (64) disposed in said compartment (48) adjacent to said heat sync for directing heated air adjacent to said heat sink (58) out of said exhaust outlets (62), said side faces (46) of said chassis (38) each defining an air inlet (66) for allowing ambient air to enter said compartment (48),
    a power source (78) electrically connected with said cooling element (56) and said temperature controller (72) and said sensor (76) for powering said cooling element (56) and said temperature controller (72),
    a graphical user interface having a rectangular shape connected with said frame (22) for presenting and receiving operational data related to the assembly (20).

2. An assembly (20) as set forth in claim 1 wherein said frame (22) further includes a top (84) and a front wall (86) and a rear wall (88),
    said track (36) includes a pair of tracks (36) each extending along one of said sidewalls (30) between said top (84) and said base (28) of said frame (22),
    each of said tracks (36) defines a pair of slots (90) extending therein in spaced and parallel relationship with one another and linearly along said track (36),
    said carrier (34) includes a pair of carriers (34) each having a generally U-shaped cross section and partially surrounding one of said tracks (36) and including a pair of projections (92) each slideably disposed in one of said slots (90) of said track (36) for allowing said upward and downward movement of said carrier (34) and said cold bars (26) along said track (36) and for preventing outward movement of said carrier (34) and said cold bars (26) relative to said track (36),
    a pin (94) slideably extends through said carrier (34) for engaging said track (36) to lock said carrier (34) and said cold bars (26) in a predetermined location along said track (36), said frame (22) defines a chamber (96) between said top (84) and said base (28) and said front wall (86) and said rear wall (88) and said sidewalls (30), said top (84) defines a mouth (100) extending to said chamber (96), said top (84) being defined by a padding layer (98), a pair of flanges (102) having a rectangular shape extend away from said front wall (86) of said frame (22) in spaced and parallel relationship with one another, a head rest (104) is connected with and spaced from said flanges (102) of said frame (22), said head rest (104) includes an inner cylinder (106) having a tube shape and cushion (108) having a tube shape disposed around said inner cylinder (106), a pair of rods (110) are each pivotally connected with one of said flanges (102) and said head rest (104) for providing for pivoting movement of said head rest (104) toward and away from said front wall (86) of said frame (22) relative to said flanges (102), a pair of fasteners (112) each threadedly extend through one of said flanges (102) and one of said rods (110) for tightening said head rest (104) in a fixed position, said graphical user interface includes a first graphical user interface (80) having a rectangular shape that extends perpendicularly from said front wall (86) and spaced from said flanges (102) toward said bottom for presenting and receiving operational data related to the assembly (20), said rearward face (44) of each of said chassis (38) being connected with said carrier (34) to provide for movement of said cold bars (26) along said track (36).

3. An assembly (20, 320) as set forth in claim 1 wherein each of said pommels (50) has a cylindrical shape.

4. An assembly (20, 320) as set forth in claim 3 wherein each of said pommels (450) defines a plurality of indentations (327) for receiving fingers of the patient.

\* \* \* \* \*